(12) United States Patent
Farrand et al.

(10) Patent No.: US 6,818,260 B2
(45) Date of Patent: Nov. 16, 2004

(54) THIENOTHIOPHENE DERIVATIVES

(75) Inventors: Louise Farrand, Speitsbury (GB);
Marcus Thompson, Fordinbridge (GB);
Mark Giles, Southampton (GB);
Martin Heeney, Southampton (GB);
Steven Tierney, Southampton (GB);
Maxim Shkunov, Southampton (GB);
David Sparrowe, Bournemouth (GB);
Iain McCulloch, Kings Somborne (GB)

(73) Assignee: Merck Patent GmbH, Darmstadt (DE)

( * ) Notice: Subject to any disclaimer, the term of this patent is extended or adjusted under 35 U.S.C. 154(b) by 27 days.

(21) Appl. No.: 10/190,706

(22) Filed: Jul. 9, 2002

(65) Prior Publication Data

US 2003/0021912 A1 Jan. 30, 2003

(30) Foreign Application Priority Data

Jul. 9, 2001 (EP) .............................................. 01115742

(51) Int. Cl.$^7$ ......................... C09K 19/34; C09K 19/32; C09K 19/38; C07D 495/14; C07D 333/72
(52) U.S. Cl. .............. 428/1.1; 252/299.61; 252/299.62; 252/299.3; 549/43; 549/46; 549/47; 549/48
(58) Field of Search ....................... 252/299.61, 299.62, 252/299.3; 428/1.1; 549/43, 46, 47, 48, 34, 35

(56) References Cited

U.S. PATENT DOCUMENTS 4,639,328 A   1/1987   Krause et al.
6,645,401 B2 * 11/2003  Giles et al. .................. 252/500
6,676,857 B2 *  1/2004  Heeney et al. ............... 252/500
6,695,978 B2 *  2/2004  Worrall et al. .......... 252/299.62

FOREIGN PATENT DOCUMENTS

WO     WO 99/12989      3/1999

OTHER PUBLICATIONS

Kossmehl, Gerhard et al., "Über Polyarylenalkenylene und Polyheteroarylenaikenylene, 13$^{a)}$", 1297 Makromolekulare Chemie, vol. 183 (1982).

Haristoy, D. et al., "Structure and photoconductive behaviour of a sanidic liquid crystal", Liquid Crystals, 2000, vol. 27, No. 3, pp. 321–328.

Kieboorns, Rafaël et al., "Synthesis, Electrical, and Optical Properties of Conjugated Polymers", Conducing Polymers, vol. 8, 2001.

* cited by examiner

Primary Examiner—Shean C. Wu
(74) Attorney, Agent, or Firm—Miller, White, Zelano, Branigan, P.C.

(57) ABSTRACT

The invention relates to new thienothiophene derivatives, their use as semiconductors or charge transport materials, in optical, electrooptical or electronic devices like for example organic field effect transistors (FET or OFET) for thin film transistor liquid crystal displays and integrated circuit devices such as RFID tags, electroluminescent devices in flat panel displays, and in photovoltaic and sensor devices, and to a field effect transistor, light emitting device or ID tag comprising the thienothiophene derivatives.

50 Claims, No Drawings

THIENOTHIOPHENE DERIVATIVES

FIELD OF INVENTION

The invention relates to new thienothiophene derviatives. The invention further relates to their use as semiconductors or charge transport materials, in optical, electrooptical or electronic devices like for example organic field effect transistors (FET or OFET) for thin film transistor liquid crystal displays and integrated circuit devices such as radio frequency identification (RFID) tags, electroluminescent devices in flat panel displays, and in photovoltaic and sensor devices. The invention further relates to a field effect transistor, light emitting device or identification (ID) tag comprising the new thienothiophene derivatives.

BACKGROUND AND PRIOR ART

Organic materials have recently shown promise as the active layer in organic based thin film transistors and organic field effect transistors [see H. E. Katz, Z. Bao and S. L. Gilat, *Acc. Chem. Res.*, 2001, 34, 5, 359]. Such devices have potential applications in smart cards, security tags and the switching element in flat panel displays. Organic materials are envisaged to have substantial cost advantages over their silicon analogues if they can be deposited from solution, as this enables a fast, large-area fabrication route.

The performance of the device is principally based upon the charge carrier mobility of the semiconducting material and the current on/off ratio, so the ideal semiconductor should have a low conductivity in the off state, combined with a high charge carrier mobility ($>1\times10^{-3}$ cm$^2$V$^{-1}$s$^{-1}$). In addition, it is important that the semiconducting material is relatively stable to oxidation i.e. it has a high ionisation potential, as oxidation leads to reduced device performance.

Compounds known in prior art for use as semiconductors are the fused dimer of dithienothiophene (DTT) and α,α'-bis(dithieno[3,2-b:2',3'-d]thiophene (BDT) having the structures shown below.

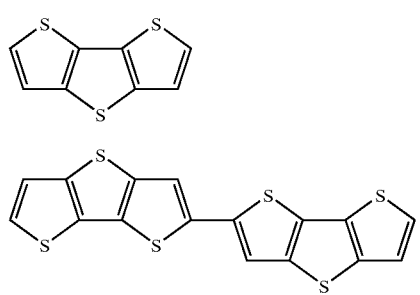

DTT

BDT

BDT and DDT are described for example in F. de Jong and M. J. Janssen, J. Org. Chem., 1971,36,12, 1645; S. Inaoka and D. M. Collard, J. Mater. Chem., 1999, 9, 1719; H. Sirringhaus et al, Appl. Phys. Lett. 1997,71 (26), 3871; X-C. Li et al, J. Am. Chem. Soc., 1998,120, 2206, and in the international patent application WO 99/12989.

In particular BDT, which has been extensively studied, has been shown to be an effective p-type semiconductor for organic FETs with a very high charge carrier mobility of 0.02–0.05 cm$^2$/V. BDT also has been found in the solid state to have a completely coplanar formation, and to be more planar than oligomers of thiophene.

However, the materials described in prior art have several disadvantages. BDT has a high melting point and is very insoluble, therefore, if used as the active layer in an organic thin film transistor, it cannot be readily solution processed.

As a result, for applications like FETs, prior art materials like BDT are usually deposited as a thin film by vacuum deposition, which is an expensive processing technique that is unsuitable for the fabrication of large-area films.

It was an aim of the present invention to provide new organic materials for use as semiconductors or charge transport materials, which are easy to synthesize, have high charge mobility, and good processibility. The materials should be easily processible to form thin and large-area films for use in semiconductor devices. Other aims of the invention are immediately evident to those skilled in the art from the following description.

It was found that these aims can be achieved by providing thienothiophenes as described below.

U.S. Pat. No. 4,639,328 discloses compounds with a thienothiophene group for use as components of liquid crystalline phases, but does not provide any suggestion to semiconductor materials.

Definition of Terms

The terms 'liquid crystalline or mesogenic material' or 'liquid crystalline or mesogenic compound' means materials or compounds comprising one or more rod-shaped, lath-shaped or disk-shaped mesogenic groups, i.e. groups with the ability to induce liquid crystal phase behaviour. The compounds or materials comprising mesogenic groups do not necessarily have to exhibit a liquid crystal phase themselves. It is also possible that they show liquid crystal phase behaviour only in mixtures with other compounds.

SUMMARY OF THE INVENTION

One object of the invention is to provide thienothiophene compounds of formula I $$R^1-Z^1-(A^1-Z^2)_m-(T-Z^3)_n-(A^2-Z^4)_o-R^2 \quad \text{I}$$

wherein
R$^1$ and R$^2$ are independently of each other H, halogen, CN, NO$_2$, straight chain, branched or cyclic alkyl with 1 to 20 C-atoms, which may be unsubstituted, mono- or poly-substituted by F, Cl, Br, I or CN, it being also possible for one or more non-adjacent CH$_2$ groups to be replaced, in each case independently from one another, by —O—, —S—, —NH—, —NR$^0$—, —SiR$^0$R$^{00}$—, —CO—, —COO—, —OCO—, —OCO—O—, —S—CO—, —CO—S—, —CH=CH— or —C≡C— in such a manner that O and/or S atoms are not linked directly to one another,
R$^0$ and R$^{00}$ are independently of each other H or alkyl with 1 to 12 C-atoms,
A$^1$ and A$^2$ are independently of each other an alicyclic or aromatic group that may also comprise one or more hetero atoms and one or more fused rings, and A$^1$ may also denote T,
Z$^1$ to Z$^4$ are independently of each other —O—, —S—, —CO—, —COO—, —OCO—, —O—COO—, —CO—NR$^0$—, —NR$^0$—CO—, —OCH$_2$—, —CH$_2$O—, —SCH$_2$—, —CH$_2$S—, —CF$_2$O—, —OCF$_2$—, —CF$_2$S—, —SCF$_2$—, —CH$_2$CH$_2$—, —CF$_2$CH$_2$—, —CH$_2$CF$_2$—, —CF$_2$CF$_2$—, —CH=N—, —N=CH—, —N=N—, —CH=CR$^0$—, —CX$^1$=CX$^2$—, —C≡C—, —CH=CH—COO—, —OCO—CH=CH— or a single bond,
X$^1$ and X$^2$ are independently of each other H, F, Cl or CN,
T is a group consisting of 3, 4, 5 or 6 thiophene rings which may also be mono- or polysubstituted by R$^1$, wherein at least 3 of the thiopene rings are fused together, m and o are independently of each other 0, 1, 2 or 3, and n is 1, 2 or 3.

Another object of the invention is the use of compounds of formula I as semiconductors or charge transport materials, in particular in optical, electrooptical or electronic devices, like for example components of integrated circuitry, field effect transistors (FET) for example as thin film transistors in flat panel display applications or for Radio Frequency Identification (RFID) tags, or in semiconducting components for organic light emitting diode (OLED) applications such as electroluminescent displays or backlights of flat panel displays, for photovoltaic or sensor devices, as electrode materials in batteries, as photoconductors and for electrophotographic applications.

Another object of the invention is a field effect transistor, for example as a component of integrated circuitry, as a thin film transistor in flat panel display applications, or in an RFID tag, comprising one or more compounds of formula I.

Another object of the invention is a semiconducting component, for example in OLED applications like electroluminescent displays or backlights of flat panel displays, in photovoltaic or sensor devices, as electrode materials in batteries, as photoconductors and for electrophotographic applications, comprising one or more compounds of formula I.

Another object of the invention is a security marking or device comprising an RFID or ID tag or a FET according to the invention.

Upon further study of the specification and appended claims, further objects and advantages of this invention will become apparent to those skilled in the art.

DETAILED DESCRIPTION OF THE INVENTION

The compounds of formula I provide several advantages over prior art materials
  by adding substituent chains and other groups they can be made more soluble, thus being suitable for spin coating or solution coating techniques, rather than vacuum deposition, to prepare thin films for use e.g. in electronic devices such as transistors,
  they can be made mesogenic or liquid crystalline, thus exhibiting a higher degree of order that leads to particularly high charge carrier mobility, in particular when being aligned in their meosphase into macroscopically uniform orientation,
  they combine the properties of a semiconducting material with those of a mesogenic material to give novel materials with a rigid, planar conjugated core and a flexible chain to increase solubility and to decrease the melting point, which show high charge-carrier mobility when being aligned in their mesophase.

The compounds of formula I are useful as charge transport semiconductors in that they have high carrier mobilities. In particular, the introduction of alkyl side chains to the thienothiophene core improves the solubility and therefore the solution processibility of the compounds of formula I.

Particularly preferred are mesogenic or liquid crystalline compounds of formula I, wherein T is a mesogenic group. These compounds are particularly useful as semiconductors or charge transport materials, as they can be processed while in the highly ordered mesophase morphology, and readily aligned by conventional techniques in a preferred direction. Both smectic and nematic mesophase ordering allows close packing of molecular pi-electron systems, which maximises intermolecular charge transfer which occurs through a hopping mechanism between adjacent molecules. In this way charge trap sites at grain boundaries between regions of different orientation are reduced.

Thus, another object of the invention is a liquid crystal mixture comprising one or more compounds of formula I and optionally comprising one or more further compounds, wherein at least one of the compounds of formula I and the further compounds is mesogenic or liquid crystalline.

It is also possible to mix compounds of formula I with other mesogenic or liquid crystal monomers that are known from prior art, in order to induce or enhance liquid crystal phase behaviour.

It is also possible to mix compounds of formula I with liquid crystal polymers or with polymerisable compounds which have one or more polymerisable groups and which may also may also be mesogenic or liquid crystalline. For example, if the compounds of formula I are mixed with one or more polymerisable mesogenic or liquid crystal compounds, the orientation as described above can be permanently "frozen-in" by polymerising the mesogens, which can also create a structure with long range order, or "monodomain". Formation of a monodomain also maximises charge transfer by eliminating charge trap sites at grain boundaries, while the polymerisation also improves the mechanical properties of the film. Further, by crosslinking the mesogens, a highly stable structure results, which has an additional advantage of being impervious to subsequent processing solvents during device fabrication, thus allowing a wider range of solvents to be used in deposition of the next layer of the device by solution techniques. In addition, it is often observed that this crosslinking further densifies the film, leading to smaller intermolecular distances and improved charge transport.

Thus, another object of the invention is a polymerisable liquid crystal mixture comprising one or more compounds of formula I and comprising one or more further polymerisable compounds, wherein the further polymerisable compounds may also be mesogenic or liquid crystalline.

Polymerisable mesogenic compounds that are suitable as comonomers are known in prior art and disclosed for example in WO 93/22397; EP 0,261,712; DE 195,04,224; WO 95/22586 and WO 97/00600.

Another object of the present invention is an anisotropic polymer film with charge transport properties obtainable from a polymerisable liquid crystal mixture as defined above that is aligned in its liquid crystal phase into macroscopically ordered orientation and polymerised or crosslinked to fix the oriented state.

Particularly preferred are liquid crystal compounds of formula I, or liquid crystal mixtures comprising one or more compounds of formula I, that exhibit a nematic and/or smectic liquid crystal phase. For FET applications smectic materials are especially preferred. For OLED applications nematic or smectic materials are especially preferred.

Particularly preferred compounds of formula I are those wherein $Z^1$, $A^1$, $Z^2$, T, $Z^3$, $A^2$ and $Z^4$ form a conjugated system. Therein $A^1$ and $A^2$ are preferably arylene or heteroarylene and $Z^1$, $Z^2$, $Z^3$ and $Z^4$ are preferably a single bond or a conjugated link like for example —C≡C— or —$CX^1$=$CX^2$—.

Further preferred compounds of formula I are those wherein
  m and o are 0,
  m and o are 1 or 2,
  T is dithienothiophene that may also be substituted with $R^1$ as defined above, n is 1 or 2 and $Z^2$ is a single bond, —$CX^1$=$CX^2$— or —C≡C—.

Particularly preferred compounds of formula I are those of the following formulae

| | |
|---|---|
| $R^1$—$Z^1$—T—$Z^3$—$R^2$ | I1 |
| $R^1$—$Z^1$—$A^1$—$Z^2$—T—$Z^3$—$R^2$ | I2 |
| $R^1$—$Z^1$—T—$Z^3$—T—$Z^3$—$R^2$ | I3 |
| $R^1$—$Z^1$—$A^1$—$Z^2$—T—$Z^3$—$A^2$—$Z^4$—$R^2$ | I4 |
| $R^1$—$Z^1$—$A^1$—$Z^2$—$A^1$—$Z^2$—T—$Z^3$—$R^2$ | I5 |
| $R^1$—$Z^1$—$A^1$—$Z^2$—T—$Z^3$—T—$Z^3$—$R^2$ | I6 |
| $R^1$—$Z^1$—T—$Z^2$—$A^1$—$Z^2$—T—$Z^3$—$R^2$ | I7 |
| $R^1$—$Z^1$—$A^1$—$Z^2$—$A^1$—$Z^2$—T—$Z^3$—$A^2$—$Z^4$—$R^2$ | I8 |
| $R^1$—$Z^1$—$A^1$—$Z^2$—$A^1$—$Z^2$—$A^1$—$Z^2$—T—$Z^3$—$R^2$ | I9 |
| $R^1$—$Z^1$—$A^1$—$Z^2$$A^1$—$Z^2$—T—$Z^3$—T—$Z^3$—$R^2$ | I10 |
| $R^1$—$Z^1$—$A^1$—$Z^2$—T—$Z^2$—$A^1$—$Z^2$—T—$Z^3$—$R^2$ | I11 |
| $R^1$—$Z^1$—$A^1$—$Z^2$—T—$Z^3$—T—$Z^3$—$A^2$—$Z^4$—$R^2$ | I12 |
| $R^1$—$Z^1$—T—$Z^2$—$A^1$—$Z^2$—$A^1$—$Z^2$—T—$Z^3$—$R^2$ | I13 |
| $R^1$—$Z^1$—$A^1$—$Z^2$—T—$Z^3$—T—$Z^3$—T—$Z^3$—$R^2$ | I14 |
| $R^1$—$Z^1$—T—$Z^2$—$A^1$—$Z^2$—T—$Z^3$—T—$Z^3$—$R^2$ | I15 |
| $R^1$—$Z^1$—$A^1$—$Z^2$—$A^1$—$Z^2$—$A^1$—$Z^2$—$A^1$—$Z^2$—T—$Z^3$—$R^2$ | I16 |
| $R^1$—$Z^1$—$A^1$—$Z^2$—$A^1$—$Z^2$—$A^1$—$Z^2$—T—$Z^3$—$A^1$—$Z^4$—$R^2$ | I17 |
| $R^1$—$Z^1$—$A^1$—$Z^2$—$A^1$—$Z^2$—T—$Z^3$—$A^2$—$Z^4$—$A^2$—$Z^4$—$R^2$ | I18 |
| $R^1$—$Z^1$—$A^1$—$Z^2$—$A^1$—$Z^2$—$A^1$—$Z^2$—T—$Z^3$—T—$Z^3$—$R^2$ | I19 |
| $R^1$—$Z^1$—$A^1$—$Z^2$—$A^1$—$Z^2$—T—$Z^2$—$A^1$—$Z^2$—T—$Z^3$—$R^2$ | I20 |
| $R^1$—$Z^1$—$A^1$—$Z^2$—T—$Z^2$—$A^1$—$Z^2$—$A^1$—$Z^2$—T—$Z^3$—$R^2$ | I21 |
| $R^1$—$Z^1$—$A^1$—$Z^2$—$A^1$—$Z^2$—T—$Z^3$—T—$Z^3$—$A^2$—$Z^4$—$R^2$ | I22 |
| $R^1$—$Z^1$—$A^1$—$Z^2$—T—$Z^2$—$A^1$—$Z^2$—T—$Z^3$—$A^2$—$Z^4$—$R^2$ | I23 |
| $R^1$—$Z^1$—T—$Z^2$—$A^1$—$Z^2$—$A^1$—$Z^2$—$A^1$—$Z^2$—T—$Z^3$—$R^2$ | I24 |
| $R^1$—$Z^1$—$A^1$—$Z^2$—$A^1$—$Z^2$—T—$Z^3$—T—$Z^3$—T—$Z^3$—$R^2$ | I25 |
| $R^1$—$Z^1$—$A^1$—$Z^2$—T—$Z^2$—$A^1$—$Z^2$—T—$Z^3$—T—$Z^3$—$R^2$ | I26 |
| $R^1$—$Z^1$—$A^1$—$Z^2$—T—$Z^2$—T—$Z^2$—$A^1$—$Z^2$—T—$Z^3$—$R^2$ | I27 |
| $R^1$—$Z^1$—$A^1$—$Z^2$—T—$Z^3$—T—$Z^3$—T—$Z^3$—$A^2$—$Z^4$—$R^2$ | I28 |
| $R^1$—$Z^1$—T—$Z^2$—$A^1$—$Z^2$—T—$Z^2$—$A^1$—$Z^2$—T—$Z^3$—$R^2$ | I29 |
| $R^1$—$Z^1$—T—$Z^2$—$A^1$—$Z^2$—$A^1$—$Z^2$—$T^1$—$Z^3$—T—$Z^3$—$R^2$ | I30 | wherein $R^1$, $R^2$, $Z^1$, $Z^2$, $Z^3$, $Z^4$ $A^1$, $A^2$ and T have, in case of multiple occurrence independently of each other, one of the meanings of formula I.

T is preferably selected from the following subformulae

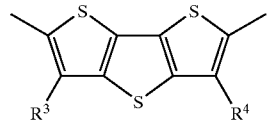

IIa

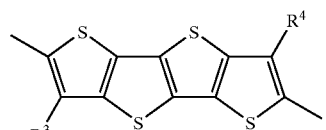

IIb

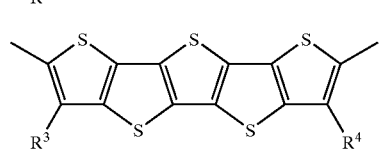

IIc

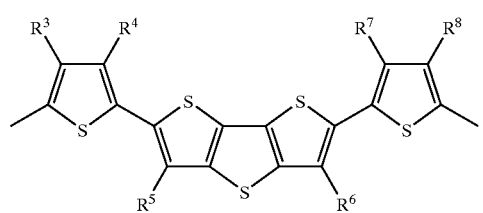

IId wherein $R^3$, $R^4$, $R^5$, $R^6$, $R^7$ and $R^8$ have independently of each other one of the meanings of $R^1$ in formula I.

Suitabl alicyclic and aromatic groups for $A^1$ and $A^2$ include 1,4-phenylene, 1,4-cyclohexylene, 1,3-doxane-2,5-diyl, 1,3-dithiane-2,5-diyl, tetrahydropyran-2,5-diyl, pyridazine-3,6-diyl or the corresponding N-oxide, piperidine-1,4-diyl, 1,4-bicyclo[2.2.2] octylene or pyrimidine-2,5-diyl, which in each case is unsubstituted or mono- or polyunsubstituted by L, with L being halogen, CN, SCN, $NO_2$, $SF_5$ or an alkyl, alkoxy, or alkylcarbonyl with 1 to 12 C atoms wherein one or more H atoms may be substituted with F or CL, or a silane or siloxy group optionally substituted by one or more alkyl groups having 1 to 12 C atoms wherein one or more H atoms may be substituted with F or Cl.

$A^1$ and $A^2$ are preferably selected from 1,4-phenylene, 1,4-cyclohexa-1,3-diene, 1,4-cyclohexenylene and in which, in addition, one or more CH groups may be replaced by N and/or one or two non-adjacent $CH_2$ groups may each be replaced by O or S, thiophene-2,5-diyl, thienothiophene-2,5-diyl, dithienothiophene-2,6-diyl, naphthalene-2,6-diyl, it being possible for all of these groups to be unsubstituted, mono- or polysubstituted by L, with L being halogen, CN, SCN, $NO_2$, $SF_5$ or an alkyl, alkoxy, alkylcarbonyl, or alkoxycarbonyl group with 1 to 12 C atoms wherein one or more H atoms may be substituted with F or Cl, or silane or siloxy groups that are optionally substituted by alkyl groups having 1 to 12 C atoms, wherein one or mor H atoms may be substituted with F or Cl.

$A^1$ and $A^2$ are particularly preferably 1,4-phenylene that is substituted with 1, 2 or 3 groups L as defined above, or thiophene-2,5-diyl, thienothiophene-2,5-diyl or dithienothiophene-2,6-diyl all of which are optionally substituted with one or more groups L as defined above.

$Z^{1-4}$ are each preferably selected from —O—, —S—, —$OCH_2$—, —$CH_2O$—, —$SCH_2$—, —$CH_2S$—, —$CF_2O$—, —$OCF_2$—, —$CF_2S$—, —$SCF_2$—, —$CH_2CH_2$—, —$CF_2CH_2$—, —$CH_2CF_2$—, —$CF_2CF_2$—, —CH=N—, —N=CH—, —N=N—, —CH=$CR^6$—, —CX$^1$=CX$^2$—, —C≡C— and a single bond, in particular from —CH=N—, —N=CH—, —N=N—, —CH=CR$^0$—, —CX$^1$=CX$^2$—, —C≡C— and a single bond.

Arylene and heteroarylene preferably denote a bivalent mono-, bi- or tricyclic aromatic or heteroaromatic group with up to 15 C atoms that may also comprise condensed rings and is optionally substituted with one or more groups R$^1$. Very preferred arylene and heteroarylene groups are those having one of the preferred meanings of A$^1$ as given above and below.

—CX$^1$=CX$^2$— is preferably —CH=CH—, —CH=CF—, —CF=CH—, —CF=CF—, —CH=C(CN)— or —C(CN)=CH—.

R$^1$ and R$^2$ in formula I are preferably alkyl or alkoxy with 1 to 25 C atoms that is optionally fluorinated.

In the formulae shown above, R$^1$ to R$^8$ are each preferably selected from C$_1$–C$_{20}$-alkyl, C$_1$–C$_{20}$-fluoroalkyl, C$_1$–C$_{20}$-alkenyl, C$_1$–C$_{20}$-alkynyl, C$_1$–C$_{20}$-alkoxy, C$_1$–C$_{20}$-thioether, C$_1$–C$_{20}$-silyl, C$_1$–C$_{20}$-ester and C$_1$–C$_{20}$-amino.

If one of R or R$^1$ to R$^8$ is an alkyl or alkoxy radical, i.e., where the terminal CH$_2$ group is replaced by —O—, this may be straight-chain or branched. It is preferably straight-chain, has 2, 3, 4, 5, 6, 7 or 8 carbon atoms and accordingly is preferably ethyl, propyl, butyl, pentyl, hexyl, heptyl, octyl, ethoxy, propoxy, butoxy, pentoxy, hexoxy, heptoxy, or octoxy, furthermore methyl, nonyl, decyl, undecyl, dodecyl, tridecyl, tetradecyl, pentadecyl, nonoxy, decoxy, undecoxy, dodecoxy, tridecoxy or tetradecoxy, for example.

Oxaalkyl, i.e., where one CH$_2$ group is replaced by —O—, is preferably straight-chain 2-oxapropyl (=methoxymethyl), 2—(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example.

Halogen is preferably F or Cl.

Particularly preferred are the following compounds

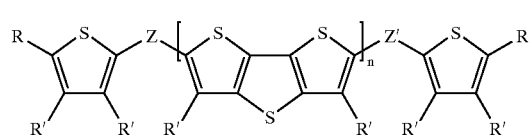
Ia

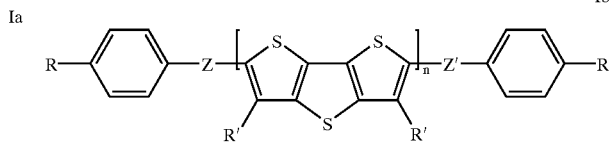
Ib

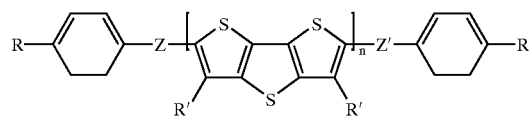
Ic

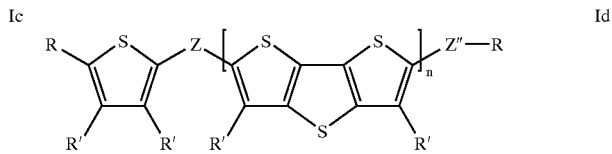
Id

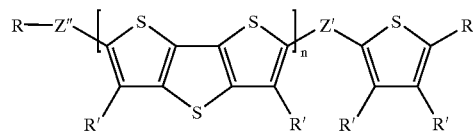
Ie

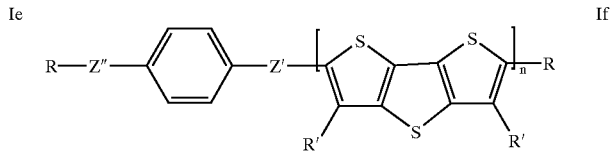
If

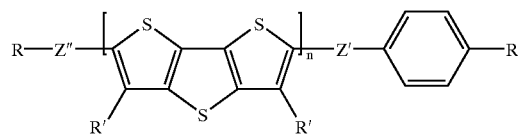
Ig

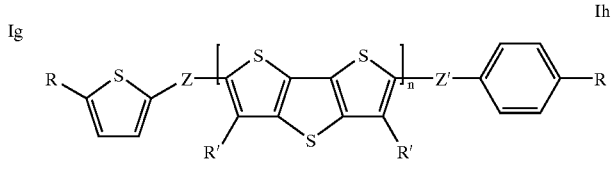
Ih

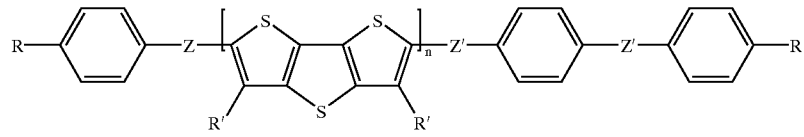
Ii

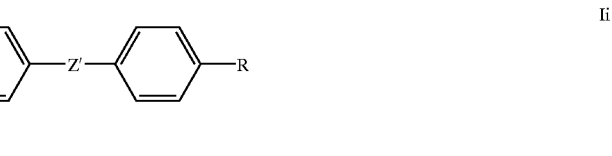

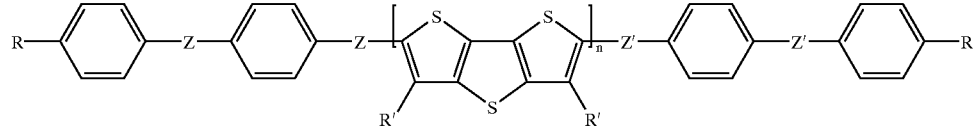
Ik

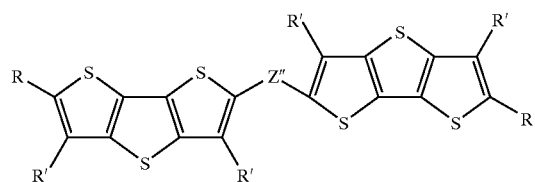
Im wherein n has the meaning of formula I,

Z and Z' have independently of each other one of the meanings of Z' in formula I, and are preferably —CH=CH—, —CH=CF—, —CF=CH—, CH=CCl—, —CCl=CH—, —CF=CF—, —CCl=CCl—, —C≡C— or a single bond, Z" has one of the meanings of $Z^1$ in formula I, and is preferably —CH=CH—, —CH=CF—, —CF=CH—, CH=CCl—, —CCl=CH—, —CF=CF—, —CCl=CCl— or —C≡C—, R and R' have independently of each other one of the meanings of $R^1$ given above, and are preferably halogen or an optionally fluorinated alkyl group with 1 to 15 C atoms.

In case one of the groups $A^{1-2}$, $Z^{1-4}$, $R^{1-8}$, R, R', $R^0$, $R^{00}$, Z', Z" and $T^1$ appears more than once in a formula as shown above and below, the multiple groups may be identical or different, unless explicitly stated otherwise.

The compounds of formula I can be synthesized according to or in analogy to methods that are known to the skilled in the art and are described for example in F. de Jong and M. J. Janssen, J. Org. Chem., 1971, 36, 12, 1645; S. Inaoka and D. M. Collard, J. Mater. Chem., 1999, 9, 1719 or WO 99/12989. Furthermore, they can be prepared according to or in analogy to the following reaction schemes. DTT and BTT can be prepared according to scheme 1.

Scheme 1

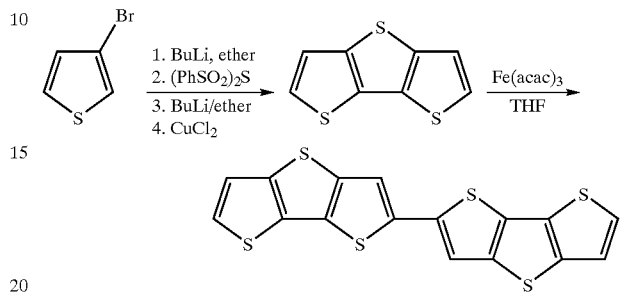

Scheme 2

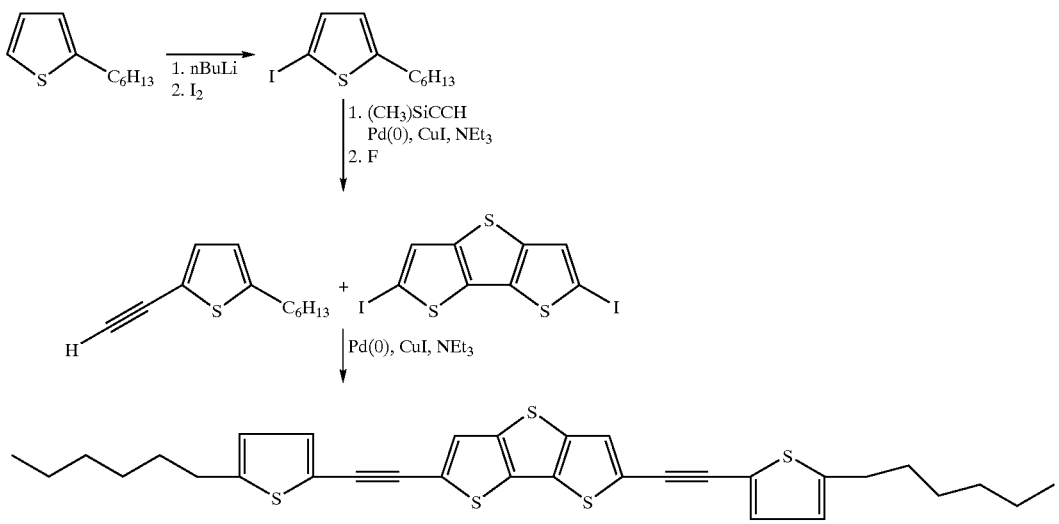

Scheme 3

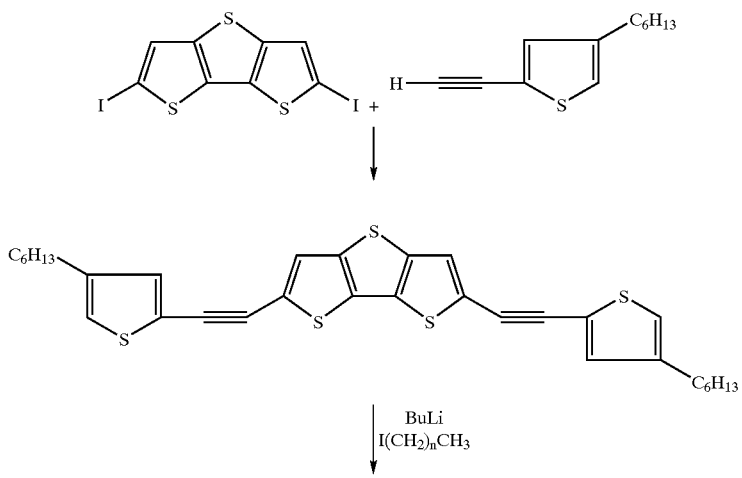

-continued
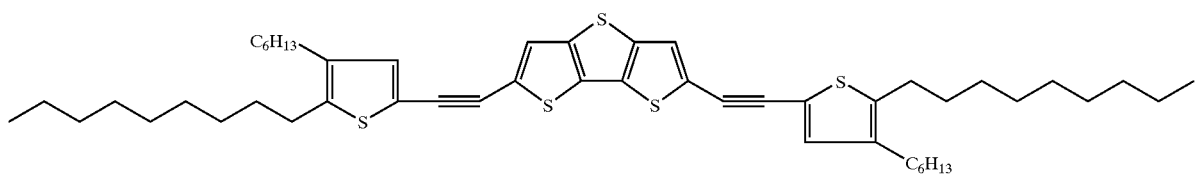
Scheme 4
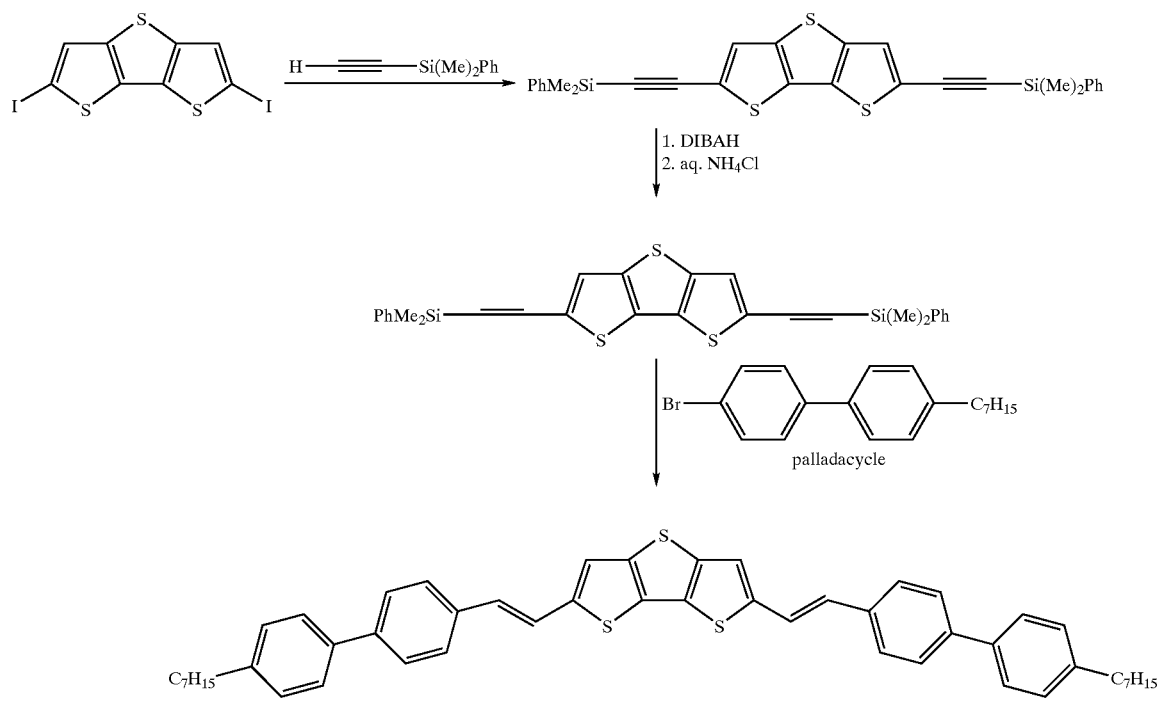
Scheme 5
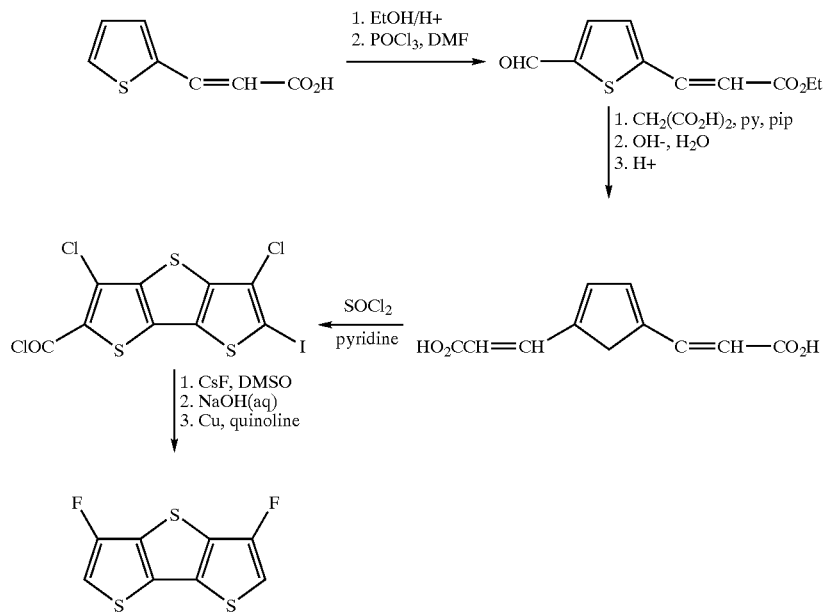

Scheme 6

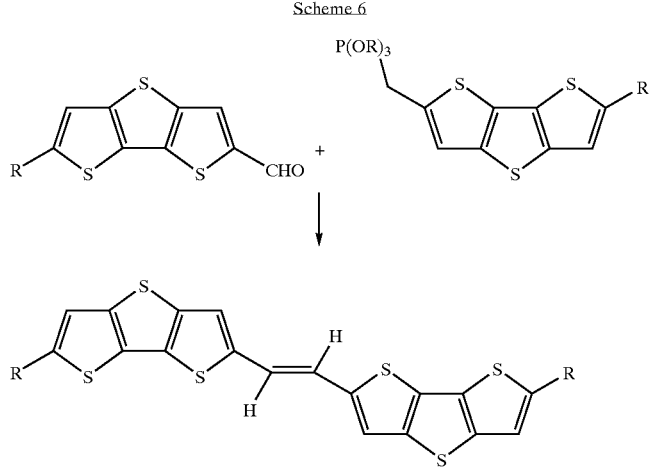

wherein R is $C_{1-20}H_{(1-20)2+1}$

Scheme 7

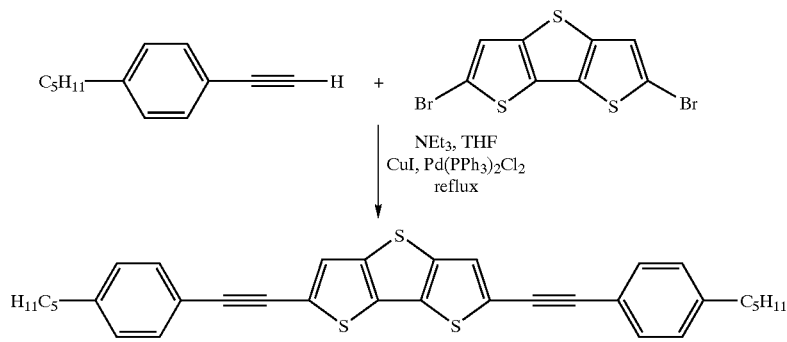

A further aspect of the invention relates to both the oxidised and reduced form of the compounds and materials according to this invention. Either loss or gain of electrons results in formation of a highly delocalised ionic form, which is of high conductivity. This can occur on exposure to common dopants. Suitable dopants and methods of doping are known to those skilled in the art, e.g. from EP 0 528 662, U.S. Pat. No. 5,198,153 or WO 96/21659.

The doping process typically implies treatment of the semiconductor material with an oxidating or reducing agent in a redox reaction to form delocalised ionic centres in the material, with the corresponding counterions derived from the applied dopants. Suitable doping methods comprise for example exposure to a doping vapor in the atmospheric pressure or at a reduced pressure, electrochemical doping in a solution containing a dopant, bringing a dopant into contact with the semiconductor material to be thermally diffused, and ion-implantantion of the dopant into the semi-conductor material.

When electrons are used as carriers, suitable dopants are for example halogens (e.g. $I_2$, $Cl_2$, $Br_2$, ICl, $ICl_3$, IBr and IF), Lewis acids (e.g. $PF_5$, $AsF_5$, $SbF_5$, $BF_3$, $BCl_3$, $SbCl_5$, $BBr_3$ and $SO_3$), protonic acids, organic acids, or amino acids (e.g. HF, HCl, $HNO_3$, $H_2SO_4$, $HClO_4$, $FSO_3H$ and $ClSO_3H$), transition metal compounds (e.g. $FeCl_3$, FeOCl, $Fe(ClO_4)_3$, $Fe(4-CH_3C_6H_4SO_3)_3$, $TiCl_4$, $ZrCl_4$, $HfCl_4$, $NbF_5$, $NbCl_5$, $TaCl_5$, $MoF_5$, $MoCl_5$, $WF_5$, $WCl_6$, $UF_6$ and $LnCl_3$ (wherein Ln is a lanthanoid), anions (e.g. $Cl^-$, $Br^-$, $I^-$, $I_3^-$, $HSO_4^-$, $SO_4^{2-}$, $NO_3^-$, $ClO_4^-$, $BF_4^-$, $PF_6^-$, $AsF_6^-$, $SbF_6^-$, $FeCl_4^-$, $Fe(CN)_6^{3-}$, and anions of various sulfonic acids, such as aryl-$SO_3^-$). When holes are used as carriers, examples of dopants are cations (e.g. $H^+$, $Li^+$, $Na^+$, $K^+$, $Rb^+$ and $Cs^+$), alkali metals (e.g., Li, Na, K, Rb, and Cs), alkaline-earth metals (e.g., Ca, Sr, and Br), $O_2$, $XeOF_4$, $(NO_2^+)$ $(SbF_6^-)$, $(NO_2^+)$ $(SbCl_6^-)$, $(NO_2^+)$ $(BF_4^-)$, $AgClO_4$, $H_2IrCl_6$, $La(NO_3)_3 \cdot 6H_2O$, $FSO_2OOSO_2F$, Eu, acetylcholine, $R_4N^+$, (R is an alkyl group), $R_4P^+$ (R is an alkyl group), $R_6As^+$ (R is an alkyl group), and $R_3S^+$ (R is an alkyl group).

The conducting form of the compounds and materials of the present invention can be used as an organic "metal" in applications, for example, but not limited to, charge injection layers and ITO planarising layers in organic light emitting diode applications, films for flat panel displays and touch screens, antistatic films, printed conductive substrates, patterns ot tracts in electronic applications such as printed circuit boards and condensers.

The mesogenic or liquid crystal compounds of formula I and the liquid crystal mixtures comprising compounds of formula I can be aligned in their liquid crystal state into homeotropic orientation, where the conjugated pi-electron systems are orthogonal to the direction of charge transport. This ensures that the intermolecular distances are minimised and hence then energy required to transport charge between molecules is minimised.

Alignment of the liquid crystal material can be achieved for example by treatment of the substrate onto which the material is coated, by shearing the material during or after coating, by application of a magnetic or electric field to the coated material, or by the addition of surface-active compounds to the liquid crystal material. Reviews of alignment techniques are given for example by I. Sage in "Thermotropic Liquid Crystals", edited by G. W. Gray, John Wiley & Sons, 1987, pages 75–77, and by T. Uchida and H. Seki in "Liquid Crystals—Applications and Uses Vol. 3", edited by B. Bahadur, World Scientific Publishing, Singapore 1992, pages 1–63. A review of alignment materials and techniques is given by J. Cognard, Mol. Cryst. Liq. Cryst. 78, Supplement 1 (1981), pages 1–77.

In case of polymerisable materials, polymerisation can be achieved by exposure to heat or actinic radiation. Actinic radiation means irradiation with light, like UV light, IR light or visible light, irradiation with X-rays or gamma rays or irradiation with high energy particles, such as ions or electrons. Preferably polymerisation is carried out by UV irradiation at a non-absorbing wavelength. As a source for actinic radiation for example a single UV lamp or a set of UV lamps can be used. When using a high lamp power the curing time can be reduced. Another possible source for actinic radiation is a laser, like e.g. a UV laser, an IR laser or a visible laser.

Polymerisation is preferably carried out in the presence of an initiator absorbing at the wavelength of the actinic radiation. For example, when polymerising by means of UV light, a photoinitiator can be used that decomposes under UV irradiation to produce free radicals or ions that start the polymerisation reaction. When curing polymerisable materials with acrylate or methacrylate groups, preferably a radical photoinitiator is used, when curing polymerisable materials with vinyl, epoxide and oxetane groups, preferably a cationic photoinitiator is used. It is also possible to use a polymerisation initiator that decomposes when heated to produce free radicals or ions that start the polymerisation. As a photoinitiator for radical polymerisation for example the commercially available Irgacure 651, Irgacure 184, Darocure 1173 or Darocure 4205 (all from Ciba Geigy AG) can be used, whereas in case of cationic photopolymerisation the commercially available UVI 6974 (Union Carbide) can be used.

The polymerisable material can additionally comprise one or more other suitable components such as, for example, catalysts, sensitizers, stabilizers, inhibitors, chain-transfer agents, co-reacting monomers, surface-active compounds, lubricating agents, wetting agents, dispersing agents, hydrophobing agents, adhesive agents, flow improvers, defoaming agents, deaerators, diluents, reactive diluents, auxiliaries, colourants, dyes or pigments.

The compounds of formula I and the mixtures obtained thereof are useful as optical, electronic and semiconductor materials, in particular as charge transport materials in field effect transistors (FETs) e.g. as components of integrated circuitry, ID tags or TFT applications. Alternatively, they may be used in organic light emitting diodes (OLEDs) in electroluminescent display applications or as backlight of e.g. liquid crystal displays, as photovoltaics or sensor materials, and for other semiconductor applications, as electrode materials in batteries, as photoconductors and for electrophotographic applications like electrophotographic recording.

FETs comprising compounds of formula I or mixtures or polymers comprising them are suitable for example as ID tags, containing specific information in clothing, food containers and other consumer products. In security applications they are suitable for use in field effect transistors for ID tags or security markings to authenticate and prevent counterfeiting of documents of value like banknotes, credit cards or ID cards, national ID documents, licenses or any product with money value, like stamps, tickets, shares, cheques etc.

The materials of the present invention are useful as optical, electronic and semiconductor materials, in particular as charge transport materials in field effect transistors (FETs), as photovoltaics or sensor materials, for electrophotographic recording, and for other semiconductor applications. Such FETs, where an organic semiconductive material is arranged as a film between a gate-dielectric and a drain and a source electrode, are generally known e.g. from U.S. Pat. No. 5,892,244, WO 00/79617, U.S. Pat. No. 5,998,804, and from the references cited in the background and prior art chapter. Due to the advantages, like low cost production using the solubility properties of the compounds according to the invention and thus the processibility of large surfaces, preferred applications of these FETs are such as integrated circuitry, TFT-displays and security applications.

Alternatively, the materials according to the invention may be used in organic light emitting devices or diodes (OLEDs), e.g. in display applications or as backlight of e.g. liquid crystal displays. Common OLEDs are realized using multilayer structures. An emission layer is generally sandwiched between one or more electron-transport and/ or hole-transport layers. By applying an electric voltage electrons and holes as charge carriers move towards the emission layer where their recombination leads to the excitation and hence luminescence of the lumophor units contained in the emission layer. The inventive compounds, materials and films may be employed in one or more of the charge transport layers and/ or in the emission layer, corresponding to their electrical and/ or optical properties. Furthermore their use within the emission layer is especially advantageous, if the compounds, materials and films according to the invention show electroluminescent properties themselves or comprise electroluminescent groups or compounds. The selection, characterization as well as the processing of suitable monomeric, oligomeric and polymeric compounds or materials for the use in OLEDs is generally known by a person skilled in the art, see e.g. Meerholz, Synthetic Materials, 111–112, 2000, 31–34, Alcala, J. Appl. Phys., 88, 2000, 7124–7128 and the literature cited therein.

According to another use, the inventive compounds, materials or films, especially those which show photoluminescent properties, may be employed as materials of light sources, e.g. of display devices such as described in EP 0 889 350 A1 or by C. Weder et al., Science, 279, 1998, 835–837.

Furthermore, the compounds of the present invention are useful as high birefringence compounds added to liquid crystalline compositions in order to increase birefringence. For this purpose, they do not need to have a mesophase themselves, but a similar shape to conventional liquid crystals in order to dissolve and not to detract from the liquid crystal properties of the composition.

In the foregoing and in the following examples, unless otherwise indicated, all temperatures are set forth uncorrected in degrees Celsius and all parts and percentages are by weight. The following abbreviations are used to illustrate the liquid crystalline phase behaviour of the compounds: K=crystalline; N=nematic; S=smectic; Ch=cholesteric; I=isotropic. The numbers between the symbols indicate the phase transition temperatures in ° C.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

EXAMPLE 1

2,6-Bis—(4-pentyl-phenylethynyl)-dithieno[3,2-b:2',3'-d]thiophene (1) was prepared according to scheme 7 and as described below

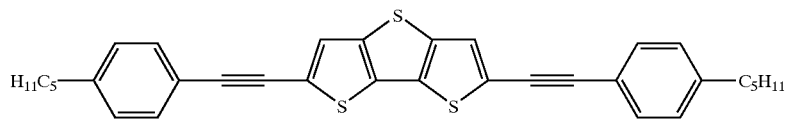

(1)

2,6-Dibromo-dithieno[3,2-b;2',3'-d]thiophene was prepared according to a procedure described in G. F. Pedulli, M. Tiecco, M. Guera, G. Martelli and P. Zanirato, J. C. S. Perkin II, 1978, 212. 2,6-Dibromo-dithieno[3,2-b;2',3'-d]thiophene (0.5 g, 1.4 mmol), triethylamine (15 ml), and a catalytic amount of palladium bis(triphenylphosphine) dichloride and copper iodide were stirred under nitrogen in tetrahydrofuran. The solution was warmed to 60° C. and 4-pentylphenyl-acetylene (1.1 g, 6.4 mmol) dissolved in tetrahydrofuran (30 ml) was added dropwise over a period of 2 hours. The solution was heated under reflux overnight. The brown solution was poured in to dichloromethane, washed with water, the chlorinated phase was removed, dried over sodium sulphate and evaporated to dryness. The residue was purified by flash column chromatography using petroleum (80–100) followed by dichloromethane as eluant. Evaporation of the appropriate fractions yielded (1) as a bright yellow solid (320 mg). $^1$H NMR and $^{13}$C NMR showed expected signals.

The following transitions and phases were observed by optical microscopy:

K-134-N-235-I (first heat)
I-234-N-110-K (first cool)
K-134-N-234-I (second heat)

EXAMPLE 2

Compound (2) was prepared as follows:

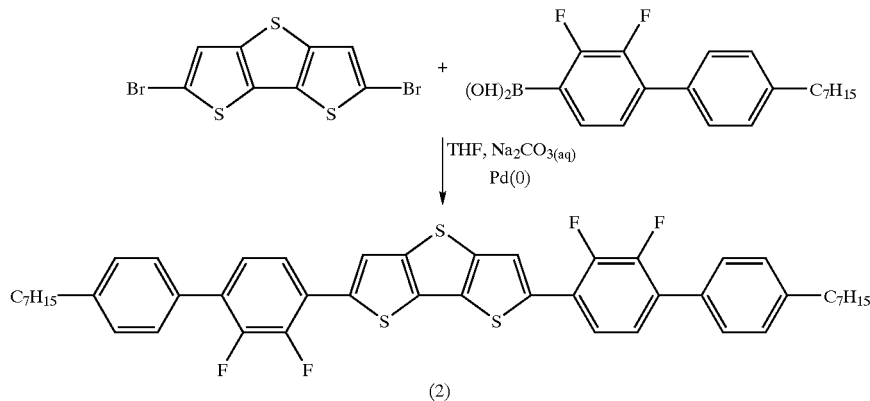

2,6-Dibromo-dithieno[3,2-b;2',3'-d]thiophene (1.0 g, 2.8 mmol) and 4'-heptylphenyl-2,3-difluorophenyl benzoic acid (2.1 g), sodium carbonate (1.07 g, 10.1 mmol in 20 ml water) and a catalytic amount of palladium bis(triphenylphosphine) dichloride were stirred under reflux in tetrahydrofuran. After 16 h, the brown solution was poured in to dichloromethane, washed with water, the chlorinated phase was removed, dried over sodium sulphate and evaporated to dryness. The residue was purified by flash column chromatography using petroleum (80–100) followed by dichloromethane as eluant. Evaporation of the appropriate fractions yielded (2) as a bright yellow solid (430 mg). $^1$H and $^{13}$C NMR showed expected signals.

The following transitions and phases were observed by optical microscopy:

K-123-N-262-I (first heat)
I-256-N-112-K (first cool)

The entire disclosure[s] of all applications, patents and publications, cited herein and of corresponding European application No. 01 115742.7, filed Jul. 9, 2001 is incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A liquid crystal mixture comprising one or more thienothiophene according to formula I, and one or more further compounds, wherein at least one of said thienothiophene compound and/or said further compounds is mesogenic or liquid crystalline, $$R^1-Z^1-(A^1-Z^2)_m-(T-Z^3)_n-(A^2-Z^4)_o-R^2 \qquad I$$

wherein
$R^1$ and $R^2$ are each independently, H, halogen, CN, NO$_2$, or straight chain, branched or cyclic alkyl with 1 to 20 C-atoms, which is unsubstituted, or mono- or poly-substituted by F, Cl, Br, I or CN, wherein optionally one or more non-adjacent CH$_2$ groups are replaced, in each case independently, by —O—, —S—, —NH—, —NR⁰—, —SiR⁰R⁰⁰—, —CO—, —COO—, —OCO—, —OCO—O—, —S—CO—, —CO—S—, —CH=CH— or —C≡C— in such a manner that O and/or S atoms are not linked directly to one another, R⁰ and R⁰⁰ are independently of each other H or alkyl with 1 to 12 C-atoms, A¹ and A² are independently of each other an alicyclic or aromatic group which optionally contains one or more hetero atoms and optionally exhibits one or more fused rings, and A¹ may also be T, Z¹ to Z⁴ are independently of each other —O—, —S—, —CO—, —COO—, —OCO—, —O—COO—, —CO—NR⁰—, —NR⁰—CO—, —OCH₂—, —CH₂O—, —SCH₂—, —CH₂S—, —CF₂O—, —OCF₂—, —CF₂S—, —SCF₂—, —CH₂CH₂—, —CH₂CF₂—, —CH₂CF₂—, —CF₂CF₂—, —CH=N—, —N=CH—, —N=N—, —CH=CR⁰—, —CX¹=CX²—, —C≡C—, —CH=CH—COO—, —OCO—CH=CH— or a single bond, X¹ and X² are independently of each other H, F, Cl or CN, T is a group consisting of 3, 4, 5 or 6 fused thiophene rings wherein at least 3 of said thiophene rifles are fused together, and which in each case are optionally mono- or polysubstituted by R¹, m and o are independently of each other 0, 1, 2 or 3, and n is 1, 2 or 3.

2. A mixture according to claim 1, wherein
T is selected from the following subformulae:

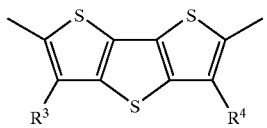
IIa

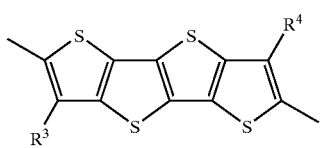
IIb

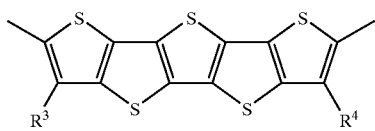
IIc

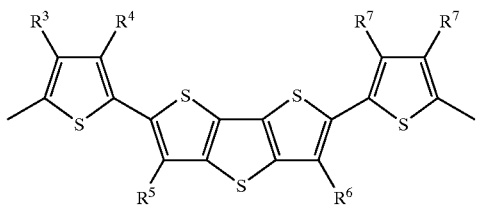
IId wherein R³, R⁴, R⁵, R⁶, R⁷ and R⁸ are each, independently, H, halogen, CN, NO₂, or straight chain, branched or cyclic alkyl with 1 to 20 C-atoms, which is unsubstituted, or mono- or poly-substituted by F, Cl, Br, I or CN, wherein optionally one or more non-adjacent CH₂ groups are replaced, in each case independently, by —O—, —S—, —NH—, —NR⁰—, —SiR⁰R⁰⁰—, —CO—, —COO—, —OCO—, —OCO—O—, —S—CO—, —CO—S—, —CH=CH— or —C≡C— in such a manner that O and/or S atoms are not linked directly to one another.

3. A mixture according to claim 1, wherein
A¹ and A² are each a group selected from 1,4-phenylene, 1,4-cyclohexa-1,3-diene, 1,4-cyclohexenylene, in which, in addition, one or more CH groups are each optionally replaced by N and/or one or two non-adjacent CH₂ groups are each optionally replaced by O or S, thiophene-2,5-diyl, thienothieophene-2,5-diyl, dithienothiophene-2,6-diyl, furan-2,5-diyl, 1,4-bicyclo-(2,2,2)-octylene, naphthalene-2,6-diyl, and indane-2,5-diyl, wherein each case the group is unsubstituted or mono- or polysubstituted by L, and L is halogen, CN, SCN, NO₂, SF₅, or an alkyl, alkoxy, alkylcarbonyl or alkoxycarbonyl group with each having up to 12 C atoms wherein in each case one or more H atoms are optionally replaced by F or Cl, or a silane or siloxy group optionally substituted by one or more alkyl groups having 1 to 12 C atoms wherein one or more H atoms are optionally replaced by F or Cl.

4. A mixture according to claim 2, wherein
A¹ and A² are each a group selected from 1,4-phenylene, 1,4-cyclohexa-1,3-diene, 1,4-cyclohexenylene, in which, in addition, one or more CH groups are each optionally replaced by N and/or one or two non-adjacent CH₂ groups are each optionally replaced by O or S, thiophene-2,5-diyl, thienothieophene-2,5-diyl, dithienothiophene-2,6-diyl, furan-2,5-diyl, 1,4-bicyclo-(2,2,2)-octylene, naphthalene-2,6-diyl, and indane-2,5-diyl, wherein each case the group is unsubstituted or mono- or polysubstituted by L, and L is halogen, CN, SCN, NO₂, SF₅ or an alkyl, alkoxy, alkylcarbonyl or alkoxycarbonyl group with each having up to 4 C atoms, wherein in each case one or more H atoms are optionally replaced by F or Cl.

5. A mixture according to claim 1, wherein R¹ to R⁸ are each selected from H, F, Cl, CN, NO₂, straight chain, branched or cyclic alkyl with 1 to 20 C-atoms, which may be unsubstituted, or mono- or poly-substituted by F, Cl, Br, I or CN, and wherein one or more non-adjacent CH₂ groups are optionally replaced, in each case independently from one another, by —O—, —S—, —NH—, —NR⁰—, —SiR⁰R⁰⁰—, —CO—, —COO—, —OCO—, —OCO—O—, —S—CO—, —CO—S—, —CH=CH— or —C≡C— in a manner whereby O and/or S atoms are not linked directly to one another.

6. A mixture according to claim 1, wherein Z¹, Z², Z³ and Z⁴ are each, independently, selected from —CH=CH—, —CH=CF—, —CF=CH—, —CF=CF—, —CH=C(CN)— or —C(CN)=CH—, —C≡C— or a single bond.

7. A mixture according to claim 1, wherein said compound of formula I is of the following formulae:

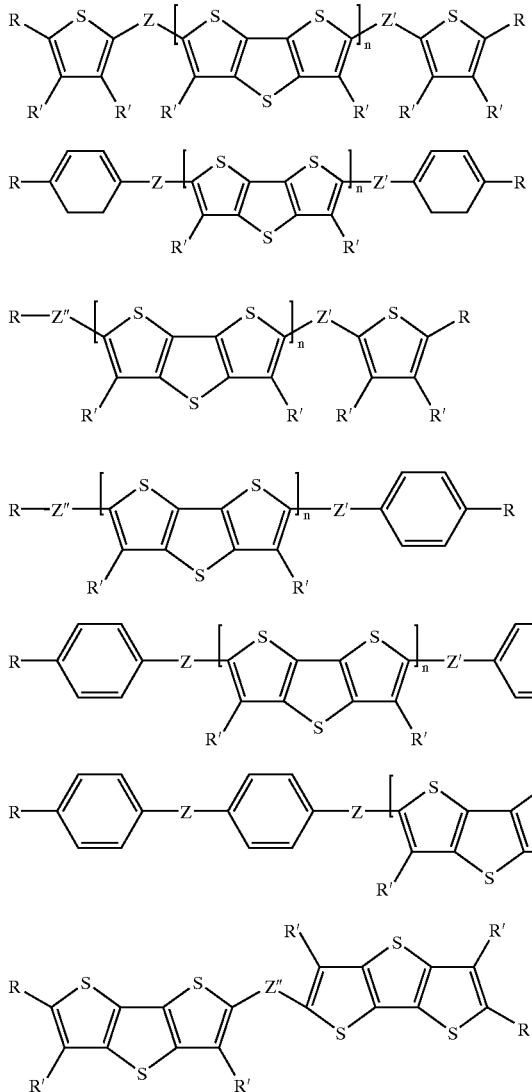
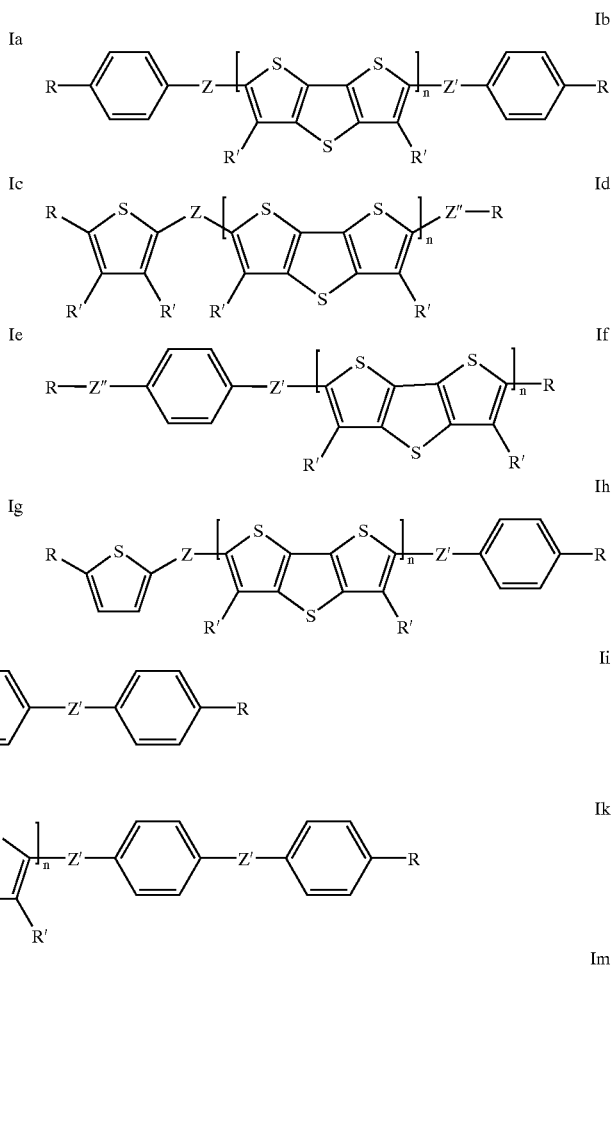

wherein n is 1, 2 or 3,

Z and Z' are each, independently, —O—, —S—, —CO—, —COO—, —OCO—, —O—COO—, —CO—NR⁰—, —NR⁰—CO—, —OCH₂—, —CH₂O—, —SCH₂—, —CH₂S—, —CF₂O—, —OCF₂—, —CF₂S—, —SCF₂—, —CH₂CH₂—, —CF₂CH₂—, —CH₂CF₂—, —CF₂CF₂—, —CH=N—, —N=CH—, —N=N—, —CH=CR⁰—, —CX¹=CX₂—, —C≡C—, —CH=CH—COO—, —OCO—CH=CH— or a single bond, Z" is —O—, —S—, —CO—, —COO—, —OCO—, —O—COO—, —CO—NR⁰—, —NR⁰—CO—, —OCH₂—, —CH₂O—, —SCH₂—, —CH₂S—, —CF₂O—, —OCF₂—, —CF₂S—, —SCF₂—, —CH₂CH₂—, —CF₂CH₂—, —CH₂CF₂—, —CF₂CF₂—, —CH=N—, —N=CH—, —N=N—, —CH=CR⁰—, —CX¹=CX²—, —C≡C—, —CH=CH—COO—, —OCO—CH=CH— or a single bond, and R and R' are each independently of each other H, halogen, CN, NO₂, or straight chain, branched or cyclic alkyl with 1 to 20 C-atoms, which is unsubstituted, or mono- or poly-substituted by F, Cl, Br, I or CN, wherein optionally one or more non-adjacent CH₂ groups are replaced, in each case independently, by —O—, —S—, —NH—, —NR⁰—, —SiR⁰R⁰⁰—, —CO—, —COO—, —OCO—, —OCO—O—, —S—CO—, —CO—S—, —CH=CH— or —C≡C— in such a manner that O and/or S atoms are not linked directly to one another.

8. A mixture according to claim 7, wherein Z' and Z" are each independently, —CH=CH—, —CH=CF—, —CF=CH—, CH=CCl—, —CCl=CH—, —CF=CF—, —CCl=CCl—, —C≡C— or a single bond.

9. A mixture according to claim 7, wherein Z" is —CH=CH—, —CH=CF—, —CF=CH—, CH=CCl—, —CCl=CH—, —CF=CF—, —CCl=CCl—, —C≡C— or a single bond.

10. A mixture according to claim 8, wherein Z" is —CH=CH—, —CH=CF—, —CF=CH—, CH=CCl—, —CCl=CH—, —CF=CF—, —CCl=CCl—, —C≡C— or a single bond.

11. A mixture according to claim 7, wherein R and R' are each independently halogen or an optionally fluorinated alkyl group with 1 to 15 C atoms.

12. A mixture according to claim 1, wherein said compound of formula I is mesogenic.

13. A mixture according to claim 1, wherein said compound of formula I is liquid crystalline.

14. In an optical, electrooptical or electronic device containing a semiconductor or charged transport material, the improvement wherein said semiconductor material or charged transport material comprises at least one mixture according to claim 1.

15. A device according to claim 14, wherein said device is a field effect transistor.

16. A device according to claim 14, wherein said device is a radio frequency identification tag.

17. A device according to claim 14, wherein said device is an organic light emitting diode.

18. A device according to claim 14, wherein said device is an electro-luminescent display device.

19. A device according to claim 14, wherein said device is a photovoltaic or sensor, a photoconductor, or electrophotographic recording device.

20. A mixture according to claim 1, wherein said compound of formula I is oxidatively or reductively to form a conducting ionic species.

21. In a charged injection layer, planarising layer, antistatic film or conducting substrate or pattern for electronic applications or flat panel displays, containing a mixture containing a conducting ionic species, the improvement wherein the mixture is in accordance with claim 20.

22. In an optical, electrooptical or electronic device containing a semiconductor or charge transport material, for example, components of integrated circuitry, field effect transistors (FET) for example as thin film transistors in flat panel display applications or for Radio Frequency Identification (RFID) tags, and in semiconducting components for organic light emitting diode (OLED) applications, electroluminescent display devices, backlights, photovoltaic or sensor devices, as electrode materials in batteries, as photoconductors and for electrophotographic applications, the improvement wherein said device contains a mixture of claim 1.

23. A thienothiophene of formula I

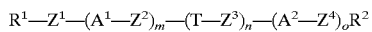

wherein $R^1$ and $R^2$ are each independently halogen, CN, $NO_2$, straight chain, branched or cyclic alkyl with 1 to 20 C-atoms, which is unsubstituted, or mono- or polysubstituted by F, Cl, Br, I or CN, wherein optionally one or more non-adjacent $CH_2$ groups to be replaced, in each case independently, by —O—, —S—, —NH—, —NR°—, —SiR°R°°—, —CO—, —COO—, —OCO—, —OCO—O—, —S—CO—, —CO—S—, —CH=CH— or —C≡C— in such a manner that O and/or S atoms are not linked directly to one another, R° and R°° are independently of each other H or alkyl with 1 to 12 C-atoms, $A^1$ and $A^2$ are independently of each other an alicyclic or aromatic group which optionally contains one or more hetero atoms and optionally exhibits one or more fused rings, and $A^1$ may also be T, $Z^1$ to $Z^4$ are independently of each other —O—, —S—, —CO—, —COO—, —OCO—, —O—COO—, —CO—NR°—, —NR°—CO—, —OCH_2—, —CH_2O—, —SCH_2—, —CH_2S—, —CF_2O—, —OCF_2—, —CF_2S—, —SCF_2—, —CH_2CH_2—, —CF_2CH_2—, —CH_2CF_2—, —CF_2CF_2—, —CH=N—, —N=CH—, —N=N—, —CH=CR°—, —CX^1=CX^2—, —C≡C—, —CH=CH—COO—, —OCO—CH=CH— or a single bond, $X^1$ and $X^2$ are independently of each other H, F, Cl or CN, T is a group consisting of 3, 4, 5 or 6 fused thiophene rings wherein at least 3 of said thiophene rings are fused together, and which in each case are optionally mono- or polysubstituted by $R^1$, m and o are independently of each other 1, 2 or 3, and n is 1, 2 or 3, with the provisos that a) $A^1$ and $A^2$ are not 1,2- or 1,3-phenylene, and b) m and o are 2 or 3, or $Z^2$ and $Z^3$ are independently of each other —CH=N—, —N=CH—, —N=N—, —CH=CR°—, —CX^1=CX^2— or —C≡C—, or both.

24. A compound according to claim 23, wherein said compound is mesogenic or liquid crystalline.

25. A compound according to claim 23, wherein said compound is selected from the following subformulae:

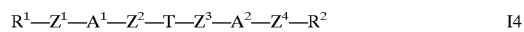 I4

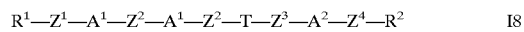 I8

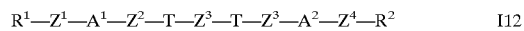 I12

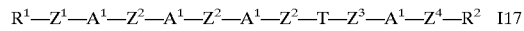 I17

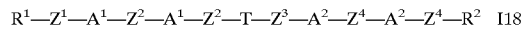 I18

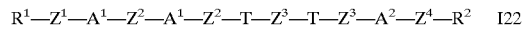 I22

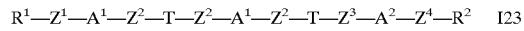 I23

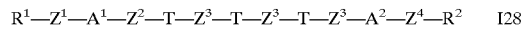 I28 wherein $R^1$, $R^2$, $Z^1$, $Z^2$, $Z^3$, $Z^4$, $A^1$, $A^2$ and T have, in case of multiple occurrence independently of each other, one of the meanings of formula I.

26. A compound according to claim 23, wherein T is selected from the following subformulae:

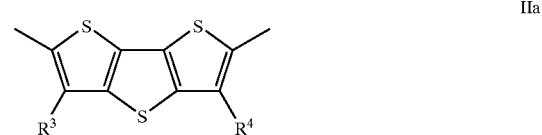

IIa

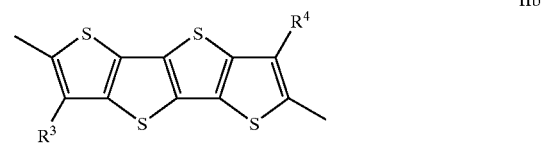

IIb

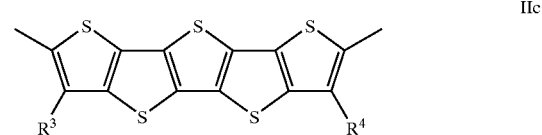

IIc

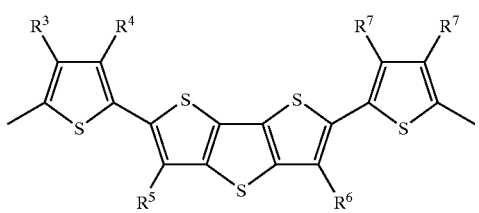

wherein $R^3$, $R^4$, $R^5$, $R^6$, $R^7$ and $R^8$ independently of each other are H or have one of the meanings of $R^1$ in formula I.

27. A compound according to claim 26, wherein T is of formula IIa.

28. A compound according to claim 23, wherein $A^1$ and $A^2$ are selected from 1,4-phenylene in which, in addition, one or more CH groups are each optionally replaced by N, thiophene-2,5-diyl, thienothiophene-2,5-diyl, dithienothiophene-2,6-diyl, furan-2,5-diyl, naphthalene-2,6-diyl and indane-2,5-diyl, wherein in each case the group is unsubstituted, mono- or polysubstituted by L, and L is halogen, CN, SCN, $NO_2$, $SF_5$ or an alkyl, alkoxy, alkylcarbonyl or alkoxycarbonyl group with each having up to 12 C atoms wherein one or more H atoms are optionally replaced by F or Cl, or a silane or siloxy group optionally substituted by one or more alkyl groups having 1 to 12 C atoms, wherein one or more H atoms are optionally replaced by F or Cl.

29. A compound according to claim 23, wherein $Z^1$, $Z^2$, $Z^3$ and $Z^4$ are selected from —CH=N—, —N=CH—, —N=N—, —CH=CR°—, —CX¹=CX²—, —C≡C—, —CH=CH—COO—, —OCO—CH=CH— or a single bond.

30. A compound according to claim 29, wherein $Z^1$, $Z^2$, $Z^3$ and $Z^4$ are selected from —CH=CH—, —CH=CF—, —CF=CH—, —CF=CF—, —CH=C(CN)— or —C(CN)=CH—, —C≡C— or a single bond.

31. A compound according to claim 23, wherein said compound is selected from the following formulae:

wherein n is 1, 2 or 3,

Z and Z' are independently of each other —O—, —S—, —CO—, —COO—, —OCO—, —O—COO—, —CO—NR°—, —NR°—CO—, —OCH₂—, —CH₂O—, —SCH₂—, —CH₂S—, —CF₂O—, —OCF₂—, —CF₂S—, —SCF₂—, —CH₂CH₂—, —CF₂CH₂—, —CH₂CF₂—, —CF₂CF₂—, —CH=N—, —N=CH—, —N=N—, —CH=CR°—, —CX¹=CX²—, —C≡C—, —CH=CH—COO—, —OCO—CH=CH— or a single bond, R and R' are independently of each other halogen, CN, $NO_2$, straight chain, branched or cyclic alkyl with 1 to 20 C-atoms, which is unsubstituted, or mono- or polysubstituted by F, Cl, Br, I or CN, wherein optionally one or more non-adjacent $CH_2$ groups to be replaced, in each case independently, by —O—, —S—, —NH—, —NR°—, SiR°R°°—, —CO—, —COO—, —OCO—, —OCO—O—, —S—CO—, —CO—S—, —CH=CH— or —C≡C— in such a manner that O and/or S atoms are not linked directly to one another, $R^1$ and $R^{00}$ are independently of each other H or alkyl with 1 to 12 C-atoms, $X^1$ and $X^2$ are independently of each other H, F, Cl or CN.

32. A compound according to claim 31, wherein n is 1.

33. A compound according to claim 31, wherein Z and Z' are selected from —CH=N—, —N=CH—, —N=N—, —CH=CR°—, —CX¹=CX²—, —C≡C— or a single bond.

34. A compound according to claim 31, wherein Z and Z' are —C≡C—, —CH=CH— or a single bond.

35. A compound according to claim 31, wherein R is an optionally fluorinated alkyl or alkoxy group with 1 to 15 C atoms.

36. A compound according to claim 31, wherein R' is an optionally fluorinated alkyl or alkoxy group with 1 to 15 C atoms.

37. A compound according to claim 31, wherein R' is H.

38. A compound according to claim 31, wherein said compound is selected of formula Ia, Ib or Ik.

39. A compound according to claim 31, wherein all groups Z and Z' denote —C≡C or all groups Z and Z' denote a single bond.

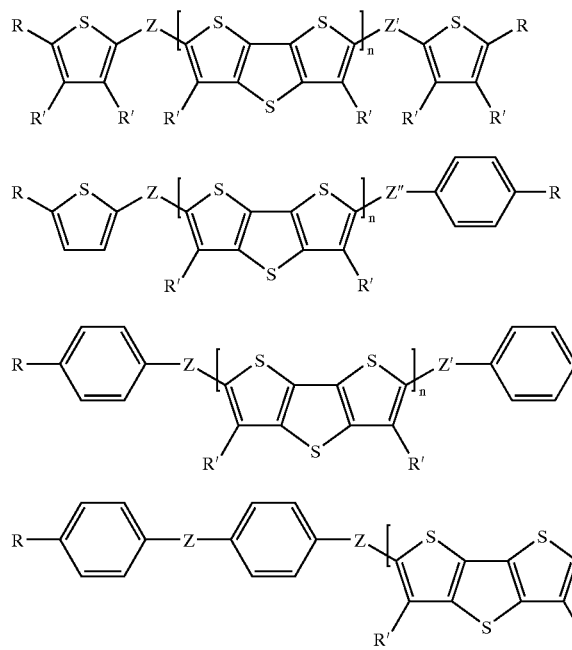

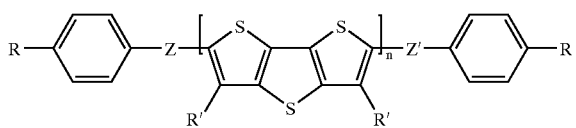

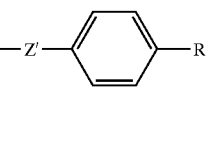

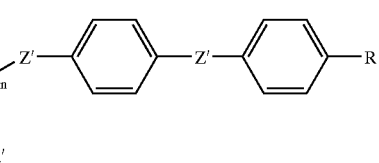

40. A compound according to claim 23, wherein said compound exhibits a nematic or smectic liquid crystal phase.

41. A liquid crystal mixture comprising one or more thienothiophene according to claim 23, and one or more further compounds, wherein at least one of said thienothiophene compound and/or said further compounds is mesogenic or liquid crystalline.

42. A liquid crystal mixture according to claim 41, wherein the mesogenic or liquid crystal compounds are aligned in their liquid crystal state into homeotropic orientation.

43. A liquid crystal mixture according to claim 1, wherein said mixture exhibits a nematic or smectic liquid crystal phase.

44. A liquid crystal mixture according to claim 1, wherein the mesogenic or liquid crystal compounds are aligned in their liquid crystal state into homeotropic orientation.

45. A liquid crystal mixture according to claim 1, further comprising one or more liquid crystal polymers or one or more polymerisable compounds which are optionally mesogenic or liquid crystalline.

46. A liquid crystal mixture according to claim 41, further comprising one or more liquid crystal polymers or one or more polymerisable compounds which are optionally mesogenic or liquid crystalline.

47. An anisotropic polymer film with charge transport properties, obtainable from a mixture according to claim 45 that is aligned in its liquid crystal phase into macroscopically ordered orientation and polymerised or crosslinked to fix the oriented state.

48. An anisotropic polymer film with charge transport properties, obtainable from a mixture according to claim 46 that is aligned in its liquid crystal phase into macroscopically ordered orientation and polymerised or crosslinked to fix the oriented state.

49. A thienothiophene of formula I:

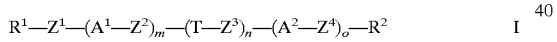
$$R^1-Z^1-(A^1-Z^2)_m-(T-Z^3)_n-(A^2-Z^4)_o-R^2 \quad\quad I$$

wherein $R^1$ and $R^2$ are each independently halogen, CN, $NO_2$, straight chain, branched or cyclic alkyl with 1 to 20 C-atoms, which is unsubstituted, or mono- or polysubstituted by F, Cl, Br, I or CN, wherein optionally one or more non-adjacent $CH_2$ groups to be replaced, in each case independently, by —O—, —S—, —NH—, —$NR^0$—, —$SiR^0R^{00}$—, —CO—, —COO—, —OCO—, —OCO—O—, —S—CO—, —CO—S—, —CH=CH— or —C≡C— in such a manner that O and/or S atoms are not linked directly to one another, $R^0$ and $R^{00}$ are independently of each other H or alkyl with 1 to 12 C-atoms, $A^1$ and $A^2$ are independently of each other 1,4-phenylene in which, in addition, one or more CH groups are each optionally replaced by N, thiophene-2,5-diyl, thienothiophene-2,5-diyl, dithienothiophene-2,6-diyl, furan-2,5-diyl, naphthalene-2,6-diyl and indane-2,5-diyl, wherein in each case the group is unsubstituted, mono- or polysubstituted by L, and L is halogen, CN, SCN, $NO_2$, $SF_5$ or an alkyl, alkoxy, alkylcarbonyl or alkoxycarbonyl group with each having up to 12 C atoms wherein one or more H atoms are optionally replaced by F or Cl, or a silane or siloxy group optionally substituted by one or more alkyl groups having 1 to 12 C atoms, wherein one or more H atoms are optionally replaced by F or Cl, $Z^1$ is —O—, —S—, —CO—, —COO—, —OCO—, —O—COO—, —CO—$NR^0$—, —$NR^0$—CO—, —$OCH_2$—, —$CH_2O$—, —$SCH_2$—, —$CH_2S$—, —$CF_2O$—, —$OCF_2$—, —$CF_2S$—, —$SCF_2$—, —$CH_2CH_2$—, —$CF_2CH_2$—, —$CH_2CF_2$—, —$CF_2CF_2$—, —CH=N—, —N=CH—, —N=N—, —CH=$CR^0$—, —$CX^1$=$CX^2$—, —C≡C—, —CH=CH—COO—, —OCO—CH=CH— or a single bond, $Z^2$ is —CH=N—, —N=CH—, —N=N—, —CH=$CR^0$—, —$CX^1$=$CX^2$— or —C≡C—, $Z^3$ is —CH=N—, —N=CH—, —N=N—, —CH=$CR^0$—, —$CX^1$=$CX^2$— or —C≡C—, $Z^4$ is —O—, —S—, —CO—, —COO—, —OCO—, —O—COO—, —CO—$NR^0$—, —$NR^0$—CO—, —$OCH_2$—, —$CH_2O$—, —$SCH_2$—, —$CH_2S$—, —$CF_2O$—, —$OCF_2$—, —$CF_2S$—, —$SCF_2$—, —$CH_2CH_2$—, —$CF_2CH_2$—, —$CH_2CF_2$—, —$CF_2CF_2$—, —CH=N—, —N=CH—, —N=N—, —CH=$CR^0$—, —$CX^1$=$CX^2$—, —C≡C—, —CH=CH—COO—, —OCO—CH=CH— or a single bond, $X^1$ and $X^2$ are independently of each other H, F, Cl or CN, T is a group consisting of 3, 4, 5 or 6 fused thiophene rings wherein at least 3 of said thiophene rings are fused together, and which in each case are optionally mono- or polysubstituted by $R^1$, m and o are independently of each other 1, 2 or 3, and n is 1, 2 or 3.

50. A thienothiophene of formula I:

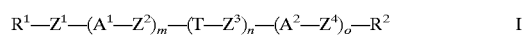
$$R^1-Z^1-(A^1-Z^2)_m-(T-Z^3)_n-(A^2-Z^4)_o-R^2 \quad\quad I$$

wherein $R^1$ and $R^2$ are each independently halogen, CN, $NO_2$, straight chain, branched or cyclic alkyl with 1 to 20 C-atoms, which is unsubstituted, or mono- or polysubstituted by F, Cl, Br, I or CN, wherein optionally one or more non-adjacent $CH_2$ groups to be replaced, in each case independently, by —O—, —S—, —NH—, —$NR^0$—, —$SiR^0R^{00}$—, —CO—, —COO—, —OCO—, —OCO—O—, —S—CO—, —CO—S—, —CH=CH— or —C≡C— in such a manner that O and/or S atoms are not linked directly to one another, $R^0$ and $R^{00}$ are independently of each other H or alkyl with 1 to 12 C-atoms, $A^1$ and $A^2$ are independently of each other 1,4-phenylene in which, in addition, one or more CH groups are each optionally replaced by N, thiophene-2,5-diyl, thienothiophene-2,5-diyl, dithienothiophene-2,6-diyl, furan-2,5-diyl, naphthalene-2,6-diyl and indane-2,5-diyl, wherein in each case the group is unsubstituted, mono- or polysubstituted by L, and L is halogen, CN, SCN, $NO_2$, $SF_5$ or an alkyl, alkoxy, alkylcarbonyl or alkoxycarbonyl group with each having up to 12 C atoms wherein one or more H atoms are optionally replaced by F or Cl, or a silane or siloxy group optionally substituted by one or more alkyl groups having 1 to 12 C atoms, wherein one or more H atoms are optionally replaced by F or Cl, $Z^1$ to $Z^4$ are independently of each other —O—, —S—, —CO—, —COO—, —OCO—, —O—COO—, —CO—NR⁰—, —NR⁰—CO—, —OCH₂—, —CH₂O—, —SCH₂—, —CH₂S—, —CF₂O—, —OCF₂—, —CF₂S—, —SCF₂—, —CH₂CH₂—, —CF₂CH₂—, —CH₂CF₂—, —CF₂CF₂—, —CH=N—, —N=CH—, —N=N—, —CH=CR⁰—, —CX¹=CX²—, —C≡C—, —CH=CH—COO—, —OCO—CH=CH— or a single bond, $X^1$ and $X^2$ are independently of each other H, F, Cl or CN, T is a group consisting of 3, 4, 5 or 6 fused thiophene rings wherein at least 3 of said thiophene rings are fused together, and which in each case are optionally mono- or polysubstituted by $R^1$, m and o are independently of each other 2 or 3, and n is 1, 2 or 3.

* * * * *

UNITED STATES PATENT AND TRADEMARK OFFICE
CERTIFICATE OF CORRECTION

PATENT NO.    : 6,818,260 B2
DATED         : November 16, 2004
INVENTOR(S)   : Louise Farrand It is certified that error appears in the above-identified patent and that said Letters Patent is hereby corrected as shown below:

<u>Title page,</u>
Item [74], *Attorney, Agent or Firm*, "Miller" should read -- Millen --.

<u>Column 21,</u>
Line 54, reads "$CX_2$" should read -- $CX^2$ --.

<u>Column 26,</u>
Line 20, reads "$R_1$" should read -- $R^0$ --.

Signed and Sealed this

Seventh Day of June, 2005

JON W. DUDAS
*Director of the United States Patent and Trademark Office*